United States Patent [19]

Zee-Cheng et al.

[11] Patent Number: 4,665,071
[45] Date of Patent: May 12, 1987

[54] 3,6-DISUBSTITUTED-1,8-NAPHTHALIMIDES AND METHODS FOR THEIR PRODUCTION AND USE

[75] Inventors: Robert K. Zee-Cheng, Shawnee; Chia C. Cheng, Leawood, both of Kans.

[73] Assignee: Warner-Lambert Company, Morris Plains, N.J.

[21] Appl. No.: 692,986

[22] Filed: Jan. 22, 1985

Related U.S. Application Data

[60] Division of Ser. No. 581,594, Feb. 21, 1984, which is a continuation-in-part of Ser. No. 481,122, Apr. 1, 1983, Pat. No. 4,499,266.

[51] Int. Cl.⁴ .................... A61K 31/535; A61K 31/44
[52] U.S. Cl. ...................................... 514/237; 514/296
[58] Field of Search ................. 424/258; 514/296, 237

[56] References Cited

U.S. PATENT DOCUMENTS 3,940,398 2/1976 Wade et al. ........................... 546/99
4,146,720 3/1979 Roldan et al. ........................ 546/99

Primary Examiner—Jerome D. Goldberg
Attorney, Agent, or Firm—Krass & Young

[57] ABSTRACT

Chemical compounds are provided that are novel 3,6-disubstituted-1,8-naphthalimides (I), as well as methods for their production, pharmaceutical compositions comprising the compounds, and methods of treatment using the compounds in dosage form. Compounds of the invention have pharmacological properties and are useful antimicrobial agents and antitumor agents.

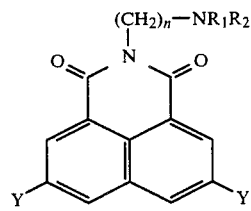

4 Claims, No Drawings

3,6-DISUBSTITUTED-1,8-NAPHTHALIMIDES AND METHODS FOR THEIR PRODUCTION AND USE

CROSS-REFERENCE TO RELATED APPLICATION

This application is a division of application Ser. No. 581,594, filed Feb. 21, 1984, which is a continuation-in-part of Ser. No. 481,122, filed Apr. 1, 1983, issued as U.S. Pat. No. 4,499,266 on Feb. 12, 1985.

TECHNICAL FIELD

The invention relates to novel 3,6-disubstituted-1,8-naphthalimides, to methods for their production, to pharmaceutical compositions comprising the compounds, and to methods of treatment using the compounds in dosage form. The compounds of the invention have pharmacological properties and are useful antimicrobial agents.

BACKGROUND OF THE INVENTION

N-substituted 3-nitro-1,8-phthalimides are known as described in the literature, for example, U.S. Pat. No. 4,146,720, inter alia.

SUMMARY OF THE INVENTION

The invention in one aspect relates to 3,6-disubstituted-1,8-naphthalimide compounds having in free base form the structural formula I:

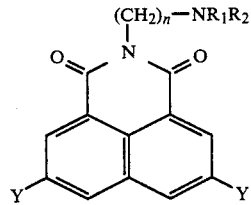

and the pharmaceutically acceptable salts thereof, where n is 2 or 3, $R_1$ and $R_2$ are H, lower alkyl, lower hydroxyalkyl, pyrrolidinyl, morpholino, or piperidinyl, and Y is $NO_2$ or $NH_2$. The terms lower alkyl or hydroxyalkyl as used herein refer to such groups containing 1 to 6 alkyl carbon atoms.

The compounds of the invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms with pharmaceutically acceptable solvents such as water, ethanol and the like are equivalent to the unsolvated forms for purposes of the invention.

The invention in another aspect relates to compounds having the structural formula I, and the pharmaceutically acceptable salts thereof, that are most preferred for their pharmacological properties. These compounds in free base form, have the following names:

N-[2-dimethylamino)ethyl]-3,6-dinitro-1,8-naphthalimide,
3,6-dinitro-N-[2-(pyrrolidinyl)ethyl]-1,8-naphthalimide,
N-[2-(diethylamino)ethyl]-3,6-dinitro-1,8-naphthalimide,
3,6-dinitro-N-[2-(morpholino)ethyl]-1,8-naphthalimide,
3,6-dinitro-N-[2-(piperidinyl)ethyl]-1,8-naphthalimide,
N-[2-dimethylamino)ethyl]-3,6-diamino-1,8-naphthalimide, and
3,6-diamino-N-[1-(piperidinyl)ethyl]-1,8-naphthalimide.

PROCESS FOR PREPARING THE COMPOUNDS

The invention in one process aspect comprises a process for preparing compounds having the structural formula I:

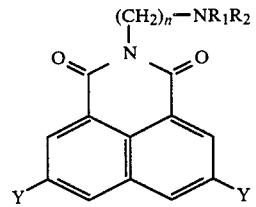

where Y is $NO_2$ by reacting 3,6-dinitro-1,8-naphthalic anhydride and an alkylenediamine having the structural formula $H_2N-(CH_2)_n-NR_1R_2$, preferably in excess, under dehydration conditions and isolating the product in free base form or pharmaceutically acceptable salt form; where n, $R_1$, and $R_2$ have the above meaning. The reaction conditions are subject to considerable variation. The reaction is conveniently carried out in an inert solvent such as toluene, at room temperature for a short period followed by reacting at reflux temperature for removal of water. The product is preferably isolated in acid addition salt form obtained by treating the free base in solution with a selected acid in solution such as methanolic HCl. The starting materials are known compounds.

Purification of compounds or products obtained by methods of the invention is accomplished in any suitable way, preferably by column chromatography or crystallization.

The invention in another aspect comprises a process for preparing compounds having the structural formula I above where Y is $NH_2$ by subjecting a compound having the structural formula I where Y is $NO_2$ to reduction and isolating the product in free base form or pharmaceutically acceptable salt form, where n, $R_1$ and $R_2$ have the above meaning. The reduction is carried out by suitable means, preferably catalytically by hydrogenation at room temperature using a palladium/-charcoal catalyst in water, or chemically by reaction with tin metal in an aqueous acidic medium at elevated temperature, preferably at temperatures in the range from about 90° to about 100° C.

The invention in its composition aspect relates to a pharmaceutical composition for treating microbial infection comprising a compound having structural formula I and the pharmaceutically acceptable salts thereof in combination with a pharmaceutically acceptable carrier.

The invention is another aspect relates to a pharmaceutical composition for treating leukemia implantable in a lower mammal, comprising a compound having structural formula I and the pharmaceutically acceptable salts thereof in combination with a pharmaceutically acceptable carrier.

The invention in another aspect relates to a pharmaceutical composition for treating solid tumors implantable in a lower mammal, comprising a compound having structural formula I and the pharmaceutically acceptable salts thereof in combination with a pharmaceutically acceptable carrier.

The invention in another method aspect relates to a method for treating microbial infections in a mammal which comprises administering a sufficient amount of a compound having structural formula I and the pharmaceutically acceptable salts thereof in combination with a pharmaceutically acceptable carrier, to mammal in need thereof.

The invention in another method aspect relates to a method for treating implantable leukemia in a lower mammal which comprises administering a sufficient amount of compound having structural formula I and the pharmaceutically acceptable salts thereof in combination with a pharmaceutically acceptable carrier, to a mammal in need thereof.

The invention in another method aspect relates to a method for treating solid tumors implantable in a lower mammal which comprises administering a sufficient formula I and the pharmaceutically acceptable salts thereof in combination with a pharmaceutically acceptable carrier.

PHYSICAL AND PHARMACOLOGICAL PROPERTIES OF THE COMPOUNDS

The compounds of the invention are useful as pharmacological agents for the treatment of microbial infections, and for the treatment of implantable leukemia and solid tumors in lower warm-blooded animals. The activity of representative compounds of the invention was established by test protocols described below.

TEST PROTOCOLS

1. In Vitro

One test protocol is the in vitro proliferating human colon adenocarcinoma (HCA) cell screen. In this test, HCT-8 cells (HCA cell line received from Yale University) are trypsinized using trypsin-EDTA. A single cell suspension is achieved by passing the cells through a 26 gauge needle with a 20 cc syringe. A cell suspension is prepared using RPMI 1640+10% FCS+50 ug/ml gentamicin sulfate with a cell concentration of approximately 30,000 cells/ml. The cell suspension is dispensed in Linbro 24-well plates; 1 ml/well. The plates are incubated for approximately 48 hours at 37 degrees C. in a 5% $CO_2$ atmosphere. At this time test compounds are added in the appropriate concentration. Five ul of the 200 ug/ml stock solution is added to each well in a primary test. Ten ul of the appropriate dilution is added to each well for a tritration test. The plates are reincubated an additional 60-65 hours at 37 degrees C. in a 5% $CO_2$ atmosphere. The cells are lysed using a mix of cationic surfactant, glacial acetic acid and sodium chloride. Two ml of the lysed cell suspension from each well is added to 8 ml of diluent. The number of nuclei is determined using a Coulter counter (ZBI model), and a percent growth for each drug concentration is calculated. From this, an $ID_{50}$ (molar concentration of compound that results in 50% inhibition of growth) is determined.

Another test protocol utilizes the solid tumor B16 melanoma in mice. The tumor is inoculated by intraperitoneal injection. The test compounds are administered intraperitoneally once daily for nine consecutive days at various doses following tumor inoculation. A ratio of survival time for treated (T)/control (C) animals is calculated. A criterion for efficacy is a ratio T/C times 100 greater than or equal to 125. See *Cancer Therapy Reviews*, 7, 167 (1980) and references cited therein for further details and interpretation of the test.

Another test protocol is the in vitro antibacterial/antifungal (ABF) test. Compounds are tested for antimicrobial activity in an agar-disk diffusion assay, a standard microbial technique for testing antibiotics. After incubation of each culture with a test compound, a zone of inhibition is determined. The zone diameter (mm) of active compounds ranges from a minimum of 13.5 mm to as high as 60 mm, with a greater diameter reflecting higher activity. For convenience, values are reported for the gram-negative bacterial species (*Escherichia coli* 04863), two gram positive bacteria (*Bacillus subtilis* 04555 and *Streptococcus faecalis* 05045 utilizing AM-09 medium), and one mycelial fungus (*Penicillium avellaneum* M2988).

In another test protocol, growth-inhibitory effects are measured against the mouse tumor line L1210 in suspension cell culture. Cell cultures were initiated at a density of 50,000 cells/ml in medium RPMI 1630 supplemented with 10 percent fetal calf serum. Composition of this culture medium and details of the culture procedure follow the published method (Journal of the National Cancer Institute 36, 405–415, 1966). Cultures are maintained at 37 degrees in stationary suspension culture under a 95 percent air+5 percent $CO_2$ atmosphere. Test compounds are added to treated cultures at the time of initiation, and are present continually. After 72 hours, 40-fold dilutions of drug-treated and untreated control cultures are prepared in 0.9 percent NaCl solution, and cells are counted on an electronic particle counter. The growth-inhibitory effects are expressed as $ID_{50}$ values, namely, test compound inhibitory dosages or concentrations required to decrease cell count in treated cultures to 50 percent of the cell count of untreated control cultures.

2. In Vivo

Another test protocol is the in vivo lymphocytic leukemia P388 test. The animals used are either male or female $CD_2F_1$ mice, six or seven animals per test group. The tumor transplant is by intraperitoneal injection of dilute ascitic fluid containing cells of lymphocytic leukemia P388. The test compounds are administered intraperitoneally once daily for five consecutive days at various doses following tumor inoculation. The animals are weighed and survivors are recorded on a regular basis for 30 days. A compound is designated "toxic" if, at a given dose, all animals died prior to four days after the first injection of drug. A ratio of survival time for treated (T)/control (C) animals is calculated. A criterion for efficacy is a ratio T/C times 100 greater than or equal to 125. See *Cancer Chemotherapy Reports*, Part 3, 3, 1 (1972) for a comprehensive discussion of the protocol.

These test protocol procedures gave results listed in Tables 1, 2 and 3 for representative compounds of the invention having the following formula Ia

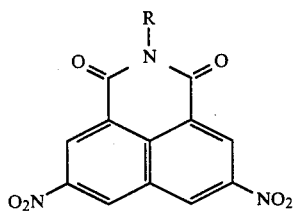

Ia where R has the meaning shown in the tables.

TABLE 1

Naphthylimide in vitro Activity vs Human Colon Adenocarcinoma

| R | $ID_{50}$ Molar |
|---|---|
| $CH_2CH_2NEt_2$ | $9.6 \times 10^{-7}$ |
| $CH_2CH_2N(CH_2)_4$ | $1.8 \times 10^{-7}$ |
| $CH_2CH_2N\overbrace{\phantom{xx}}O$ (morpholino) | $8.6 \times 10^{-7}$ |
| $CH_2CH_2N(CH_2)_5$ | $4.8 \times 10^{-7}$ |

TABLE 2

Naphthylimide Antimicrobial Activity

Inhibition Zone Diameter mm (Dose mg/ml)

| R | E. Coli | B. Subtilis | P. avellaneum | S. Faecalis |
|---|---|---|---|---|
| $CH_2CH_2N(CH_2)_4$ | 17(500) | 16(100) | 22(500) | 18(500) |
| $CH_2CH_2N\overbrace{\phantom{xx}}O$ | | 22(100) | 15(3000) | 14(500) |
| $CH_2CH_2N(CH_2)_5$ | 16(500) | 24(100) | 26(500) | 19(500) |

TABLE 3

Naphthylimide Antitumor Activity

| R | L1210 Leukemia In Vitro $ID_{50}$ Molar | Dose mg/kg | T/C × 100 (Percent) |
|---|---|---|---|
| | | P388 Leukemia In Mice | |
| $CH_2CH_2NMe_2$ | $3.6 \times 10^{-8}$ | 3.12 | 167 |
| $CH_2CH_2NEt$ | $3.5 \times 10^{-7}$ | 1.56 | 155 |
| $CH_2CH_2N(CH_2)_4$ | $8.3 \times 10^{-8}$ | | |
| $CH_2CH_2N\overbrace{\phantom{xx}}O$ | $1.1 \times 10^{-6}$ | | |
| $CH_2CH_2N(CH_2)_5$ | $2.9 \times 10^{-7}$ | | |
| | | B16 Melanoma | |
| $CH_2CH_2NMe_2$ | | 1.00 | 125 |
| $CH_2CH_2N(CH_2)_5$ | | 12.5 | 135 |

Compounds of the invention having formula I where Y is $NH_2$ typically

TABLE 3-continued

Naphthylimide Antitumor Activity

| R | L1210 Leukemia In Vitro $ID_{50}$ Molar | Dose mg/kg | T/C × 100 (Percent) |
|---|---|---|---| have comparable activity.

PREPARATION OF PHARMACEUTICAL COMPOSITIONS

When being utilized as pharmacological agents, the compounds of the invention can be prepared and administered in a wide variety of topical, oral, and parenteral dosage forms. It will be clear to those skilled in the art that the following dosage forms may comprise as the active component, one or more compounds of formula I, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the table the active compound is mixed with carrier having the necessary binding properties in suitable proportions and compacted in the shape and size desired. The powders and tablets preferably contain from 5 or 10 to about 70 percent of the active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well-known procedures. See for example Remington's Pharmaceutical Sciences, Chapter 43, 14th Ed., Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for lower mammalian subjects to be treated ranges from 0.1 mg/kg to 100 mg/kg. The preferred daily dosage range is 0.3 mg/kg to 10 mg/kg.

The invention and the best mode of practicing the same as illustrated by the following examples of preferred embodiments of selected compounds and their preparation.

EXAMPLE 1

N-[2-(Dimethylamino)ethyl]-3,6,-dinitro-1,8-naphthalimide, Hydrochloride

A mixture of 14 g (0.048 mole) of 3,6-dinitro-1,8-naphthalic anhydride and 450 ml of toluene was azeotropically refluxed for 90 min. The solution was cooled to room temperature. To this solution was added dropwise 5.6 g (0.065 mole) of unsym-N,N-dimethylethylenediamine in 7 ml of toluene. The addition took 5 min. The mixture was stirred at room temperature for 20 min., then refluxed in an oil bath at 140 degrees C. for 2 hours azeotropically. Water (1.2 ml) was collected. The reaction mixture was filtered while hot. The filtrate was washed successively with water 2×100 ml), 5% NaHCO$_3$ (2×100 ml) and water again (2×200 ml), then dried over anhydrous Na$_2$SO$_4$. To the dried filtrate was added a mixture of 40 ml of methanolic HCl (2.33 m mole HCl per 1 ml of MeOH) and 200 ml of ether with stirring. The resulting precipitate was collected by filtration, washed with ether (2×40 ml), and dried to give 12.3 g (62% yield) of the product, m.p. 296-298 degrees. An analytical sample was prepared by recrystallization from methanol, m.p. 298-300 degrees. λ (max MeOH) 268 nm (log ε 4.64), 320 (3.93), and 332 (3.95).

Anal. Calcd for C$_{16}$H$_{14}$N$_4$O$_6$.HCl.1½H$_2$O: C, 45.56; H, 4.30; N, 13.20. Found: C, 45.60; H, 4.25; N, 13.20.

EXAMPLE 2

3,6-Dinitro-N-[2-(pyrrolidinyl)ethyl]-1,8-naphthalimide Hydrocholoride

A mixture of 5.8 g (0.02 mole) of 3,6-dinitro-1,8-naphthalic anhydride in 300 ml of toluene was azeotropically refluxed for 1 hour, then cooled to room temperature. To this solution was added dropwise 2.7 g (0.024 mole) of N-(2-aminoethyl)pyrrolidine in 30 ml of toluene in 10 min. The reaction mixture was stirred at room temperature for 1 hour and refluxed azeotropically for 1 hour to remove 0.4 ml of water. The resulting brown solution was washed successively with water 3×100 ml), 5% Na$_2$CO$_3$ (2×100 ml), and again water (4×100 ml), then dried (Na$_2$SO$_4$). The aqueous washings were extracted with toluene (4×100 ml.) The latter washed with water (3×80 ml), dried and combined with the organic solution. To the toluene solution was added a mixture of 100 ml of ether and 30 ml of methanolic HCl (containing 2.33 mmole of HCl per 1 ml of MeOH). The mixture was stirred for 30 min. The resulting precipitate was collected by filtration, washed with ether (3×50 ml), and dried to give 7.3 g (87% yield) of the product, m.p. 262-264 degrees. An analytical sample was obtained by recrystallization from methanol as long needles, m.p. 294-295 degrees. λ max (MeOH) 200 nm (log ε 4.32), 264 (4.53), 320 (3.80), and 330 (3.83).

Anal. Calcd for C$_{18}$H$_{16}$N$_4$O$_6$.HCl: C, 51.37. H, 4.07.N, 13.31. Found: C, 51.30; H, 4.12; N, 13.30.

EXAMPLE 3

N-[(2-(Diethylamino)ethyl]-3,6-dinitro-1.8-naphthalimide Hydrochloride

This compound was prepared using the procedure of Example 1 from 5.8 g (0.02 mole) of 3,6-dinitro-1,8-naphthalic anhydride in 3000 ml of toluene and 2.8 g (0.024 mole) of unsym-N,N-diethylethylenediamine in 40 ml of toluene to give 6.8 g (82% yield) of the product, m.p. 235-242 degrees. An analytical sample was prepared by recrystallization from methanol as brown plates, m.p. 252-254 degrees. λ max (MeOH) 206 nm (log ε 4.37), 266 (4.56), 320 (3.86), and 332 (3.88).

Anal. Calcd for C$_{18}$H$_{18}$N$_4$O$_6$.HCl: C, 51.13; H, 4.53; N, 13.25. Found: C, 50.90; H, 4.60; N, 13.36.

EXAMPLE 4

3,6-Dinitro-N-[2-(morpholino)ethyl]-1,8-naphthalimide

This compound was prepared using the procedure for Example 1 from 5.8 g (0.02 mole) of 3,6-dinitro-1,8-naphthalic anhydride in 300 ml of toluene and 3.2 g (0.024 mole) of N-(2-aminoethyl)morpholine in 40 ml of toluene to give 4.1 g (46% yield) of the product, m.p. 250-254 degrees. An analytical sample was prepared by recrystallization from methanol as brown crystals, m.p. 275-276 degrees. λ max (MeOH) 202 nm (log ε 4.38), 265 (4.49), 318 (3.89), and 330 (3.89).

Anal. Calcd for C$_{18}$H$_{16}$N$_4$O$_7$.HCl: C, 49.49; H, 3.92; N, 12.82 Found: C, 49.60; H, 4.20; N, 12.68

EXAMPLE 5

3,6-Dinitro-N-[2-(piperidinyl)ethyl]-1,8-naphthalimide, Hydrochloride

This compound was prepared using the procedure for Example 1 from 4.3 g (0.015 mole) of 3,6-dinitronaphthalic anhydride in 250 ml of toluene and 2.4 g (0.018 mole) of N-(2-aminoethyl)piperidine in 40 ml of toluene to give 4.8 g (73% yield) of the product, m.p. 265-268 degrees. An analytical sample was prepared by crystallization from a mixture of methanol and ether, m.p. 264-266 degrees. λ max (MeOH) 202 nm (log ε 4.43), 266 (4.60), 320 (3.89) and 330 (3.92).

Anal. Calcd for C$_{19}$H$_{18}$N$_4$O$_6$.HCl: C, 52.48; H, 4.40; N, 12.88. Found: C, 52.12; H, 4.46; N, 12.70.

Using the following unsym. alkylene diamine starting materials, the following compounds are prepared by the above exemplified procedures:

| Starting Material | 3,6-Dinitro-1,8-Naphthalimide Product, as Free Base |
| --- | --- |
| H$_2$N—CH$_2$CH$_2$CH$_2$NMe$_2$ | N—[3-dimethylamino)propyl]- |
| H$_2$N—CH$_2$CH$_2$CH$_2$NEt$_2$ | N—[3-(Diethylamino)propyl]- |
| H$_2$N—CH$_2$CH$_2$CH$_2$N(CH$_2$)$_4$ | N—[3-Pyrrolidinyl)propyl]- |
| H$_2$N—CH$_2$CH$_2$CH$_2$N⟨O⟩ | N—[3-(Morpholino)propyl]- |
| H$_2$N—CH$_2$CH$_2$CH$_2$N(CH$_2$)$_5$ | N—[3-(Piperidinyl)propyl]- |

EXAMPLE 6

N-(2-Dimethylaminoethyl)-3,6-diamino-1,8-naphthalimide Hydrochloride

Method 1 (Chemical Reduction)

A mixture of 2.0 g (5 mmoles) of the hydrochloride salt of N-(dimethylaminoethyl)-3,6-dinitro-1,8-naphthalimide, 5.9 g (5.0 mmoles) of 20 mesh tin metal in 60 ml of water and 20 ml of conc. HCl was heated at 90°-100° C. for 2 hours with stirring. After cooling, the insoluble solid was removed by filtration and washed with 2×30 ml of hot water. The combined filtrate and washings were evaporated to dryness. The resulting residue was extracted with hot methanol (8×50 ml). The methanolic extracts were evaporated to dryness and the residue was triturated with 50 ml of ether, filtered and the solid washed with ether. The resulting hygroscopic solid was recrystallized from 150 ml of ethanol to give 0.4 g of the tin complex of the hydrochloride salt of the diamino compound, m.p. 190°-193°.

Additional 0.5 g of the product was obtained by concentration of the mother liquor. The total yield was 30%.

λ max (MeOH): 250 nm (log ε 4.66), 273 (4.31) and 435 (4.09).

Anal. Calcd for $C_{16}H_{18}N_4O_2 \cdot 3HCl \cdot SnCl_2$, C, 32.17; H 3.54; N. 9.38. Found: C, 32.28; H, 3.71; N. 8.90

Method 2 (Catalytic Reduction)

A mixture of 2.0 g (5 mmoles) of the hydrochloride salt of N-(dimethylaminoethyl)-3,6-dinitro-1,8-naphthalimide and 350 mg of 10% palladium-on-charcoal in 120 ml of water was hydrogenated at room temperature under 40 lbs/in$^2$ of hydrogen for one hour. Theoretical amount of hydrogen was absorbed. To the mixture was added 3 ml. of conc. HCl. It was then filtered and the filtrate was evaporated to dryness under reduced pressure. The residue was triturated with 30 ml of absolute ethanol and filtered. The resulting solid was washed with ether (5×10 ml) and dried to give 2.1 g (95% yield) of the diamino compound. Recrystallization from 150 ml of methanol gave 0.7 g (31.7% yield) of the purified product, mp. 295°–297°.

ε max (MeOH) 250 nm (log ε 4.57), 275 (4.25), 430 (3.96) and 445 (3.68). Anal. Calcd for $C_{16}H_{18}N_4O_2 \cdot 2.7HCl$: C, 48.43; H, 5.25; N, 14.12. Found C, 48.80; H, 5.21; N, 13.60.

EXAMPLE 7

N-(1-Piperidinylethyl)-3,6-diamino-1,8-naphthalimide, Hydrochloride

A mixture of 4.4 g (10 mmoles) of N-(1-piperidinylethyl)-3,6-dinitro-1,8-naphthalimide, 0.7 g of 5% palladium-on-charcoal in 180 ml of water was hydrogenated at room temperature under 40 lbs/cm$^2$ of hydrogen for 90 minutes. To the reduced mixture was added 6 ml of conc. HCl. The catalyst was removed by filtration and washed with water (3×30 ml). The combined filtrate and washings were evaporated to dryness under reduced pressure. The residue was recrystallized from a mixture of ethanol and ether. The purified crystals were collected by filtration, washed with ether, and dried to give 2.7 g mp 256°–258° (69% yield) of the hydrochloric salt of the product. λ max (MeOH): 250 nm (log ε 4.51); 275 (4.19); 430 (3.96); and 445 (3.93). Anal. Calcd for $C_{19}H_{22}N_4O_2 \cdot 1.7HCl$: C, 56.99; H, 5.96; N, 14.00. Found: C, 57.10; H, 6.00; N, 14.30.

Mass spec: M/e=338 ($C_{19}H_{22}N_4O_2$=338).

EXAMPLE 8

Preparation of Intravenous Formulations

A solution of 12.5 g of N-[2-(dimethylamino)ethyl]-3,6-dinitro-1,8-naphthalimide (from Example 1) as the hydrochloride salt is prepared in 1 liter of water for injection at room temperature with stirring. The solution is sterile filtered into 500 5-ml vials, each of which contains 2 ml of solution containing 25 mg of compound, and sealed under nitrogen.

Alternatively, after sterile filtration into vials, the water may be removed by lyophilization, and the vials then sealed aseptically, to provide a powder which is redissolved prior to injection.

Having thus described our invention, what we claim and desire by Letters Patent to secure are the following:

1. A pharmaceutical composition for treating an implantable solid tumor in a lower mammal comprising an antitumor effective amount of a compound having in free base form the structural formula I

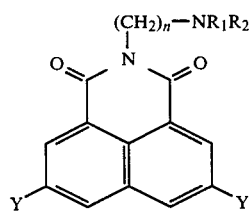

or a pharmaceutically acceptable salt thereof, where n is 2 or 3, $R_1$ and $R_2$ are H, lower alkyl, lower hydroxalkyl, pyrrolidinyl, morpholino, or piperidinyl, and Y is $NO_2$ or $NH_2$ in combination with a pharmaceutically acceptable carrier.

2. A method for treating an implantable solid tumor in a lower mammal which comprises administering an antitumor effective amount of a compound having the structural formula I according to claim 1, in combination with a pharmaceutically acceptable carrier, to a mammal in need thereof.

3. A pharmaceutical composition for treating an implantable solid tumor in a lower mammal comprising an antitumor effective amount of a compound having a free base form the structural formula I

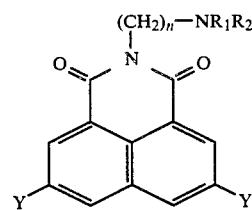

or a pharmaceutically acceptable salt thereof, where n is 2, $R_1$ and $R_2$ are lower alkyl and Y is $NO_2$ in combination with a pharmaceutically acceptable carrier.

4. A method for treating an implantable solid tumor in a lower mammal which comprises administering an antitumor effective amount of a pharmaceutical composition according to claim 3 to a mammal in need thereof.

* * * * *

UNITED STATES PATENT AND TRADEMARK OFFICE
CERTIFICATE OF CORRECTION

PATENT NO. : 4,665,071

DATED : May 12, 1987

INVENTOR(S) : Robert K. Zee-Cheng et al

It is certified that error appears in the above-identified patent and that said Letters Patent is hereby corrected as shown below:

Column 3, line 38 "acceptable carrier." should be --acceptable carrier, to a mammal in need thereof.--;

Column 4, line 22 "microbial" should be --microbiological--;

Column 6, line 32 "table" should be --tablet--;

Column 11, line 24 "$\epsilon$ max" should be --$\lambda$ max--.

Signed and Sealed this

Eighth Day of December, 1987

Attest:

DONALD J. QUIGG

Attesting Officer

Commissioner of Patents and Trademarks